US011737847B2

(12) United States Patent
Puentes et al.

(10) Patent No.: US 11,737,847 B2
(45) Date of Patent: Aug. 29, 2023

(54) SURGICAL DRAPE WITH ATTACHABLE FLUID CONTROL POUCH AND GEOMETRIC ALIGNMENT FEATURE

(71) Applicant: Allegiance Corporation, Waukegan, IL (US)

(72) Inventors: Alejandro Puentes, El Paso, TX (US); Rogelio Reyes, El Paso, TX (US); Laura E. Mott, Houston, TX (US); Caroline S. Ginn, Chesterfield, MO (US)

(73) Assignee: ALLEGIANCE CORPORATION, Waukegan, IL (US)

( * ) Notice: Subject to any disclaimer, the term of this patent is extended or adjusted under 35 U.S.C. 154(b) by 913 days.

(21) Appl. No.: 15/298,767

(22) Filed: Oct. 20, 2016

(65) Prior Publication Data
US 2017/0105807 A1    Apr. 20, 2017

Related U.S. Application Data

(60) Provisional application No. 62/244,141, filed on Oct. 20, 2015.

(51) Int. Cl.
*A61B 46/00*    (2016.01)
*A61B 46/23*    (2016.01)
*A61B 46/20*    (2016.01)

(52) U.S. Cl.
CPC .............. *A61B 46/23* (2016.02); *A61B 46/00* (2016.02); *A61B 46/40* (2016.02);
(Continued)

(58) Field of Classification Search
CPC ... A61B 46/00; A61B 46/20; A61B 2046/201; A61B 2046/205; A61B 46/23; A61B 2046/236
(Continued)

(56) References Cited

U.S. PATENT DOCUMENTS 1,597,556 A * 8/1926 Townsend .............. A61B 46/00
                                                         604/357
3,538,912 A * 11/1970 Becker ................... A61B 46/00
                                                         128/853
(Continued)

FOREIGN PATENT DOCUMENTS

| CN | 101304702 A | 11/2008 |
|----|-------------|---------|
| JP | 2015002776 A | 1/2015 |
| WO | 2014083573 A1 | 6/2015 |

OTHER PUBLICATIONS

Medline, Beach Chair Shoulder Drapes by Welmed in Drape, Beach Chair Shoulder STR 160X102 [Online], Retrieved on Oct. 14, 2015, Retrieved from the Internet: (URL: https://www.medline.com/sku/item/MDPWED12228660; ecomsessionid=MkDV3EMHYy+zZyj4eEAp1g_?skuIndex=S1&q . . . .
(Continued)

*Primary Examiner* — Adam Baker
(74) *Attorney, Agent, or Firm* — ArentFox Schiff LLP (57) ABSTRACT

A surgical drape having an attachable fluid control pouch and geometric alignment feature are described. The surgical drape may be fenestrated and include a base drape panel, an absorbent intermediate panel, and a mounting panel. The mounting panel may have a fluid impervious top surface that forms a higher quality adhesive seal with the adhesive attachment areas of the fluid control pouch. The surgical drape panels may be joined together by a continuous fluid impervious seal surrounding the fenestration. The fluid control pouch attachment edge may include a geometric structure that aligns with a corresponding geometric structure of the fenestration such that the fluid control pouch can be effectively positioned regardless of its rotational orientation relative to the surgical drape.

18 Claims, 8 Drawing Sheets

(52) U.S. Cl.
CPC ... *A61B 2046/201* (2016.02); *A61B 2046/205* (2016.02); *A61B 2046/236* (2016.02)

(58) Field of Classification Search
USPC .......................................... 128/49, 853, 854
See application file for complete search history.

(56) References Cited

U.S. PATENT DOCUMENTS

| | | | | |
|---|---|---|---|---|
| 3,766,913 | A | * | 10/1973 | Balin .................... A61B 46/00 128/853 |
| 3,902,484 | A | | 9/1975 | Winters |
| 4,024,862 | A | * | 5/1977 | Collins .................. A61B 46/00 128/854 |
| 4,869,271 | A | | 9/1989 | Idris |
| 4,890,628 | A | * | 1/1990 | Jackson ................. A61B 46/00 128/853 |
| 4,974,604 | A | * | 12/1990 | Morris ................... A61B 46/00 128/853 |
| 5,038,798 | A | | 8/1991 | Dowdy et al. |
| 5,143,091 | A | * | 9/1992 | Patnode ................ A61B 46/00 128/849 |
| 5,161,544 | A | * | 11/1992 | Morris ................... A61B 46/00 128/849 |
| 5,494,050 | A | * | 2/1996 | Reyes .................... A61B 46/27 128/849 |
| 5,618,278 | A | * | 4/1997 | Rothrum ............... A61B 46/23 128/849 |
| 5,871,014 | A | | 2/1999 | Clay et al. |
| 6,032,670 | A | * | 3/2000 | Miller .................... A61B 46/00 128/849 |
| 6,199,553 | B1 | * | 3/2001 | Hafer ..................... A61B 46/00 128/849 |
| 6,213,124 | B1 | | 4/2001 | Butterworth |
| 6,725,864 | B2 | | 4/2004 | Ewonce et al. |
| 6,923,186 | B2 | | 8/2005 | Gavette et al. |
| 7,594,512 | B2 | | 9/2009 | Reyes et al. |
| 8,424,532 | B2 | | 4/2013 | Esquivel et al. |
| 2007/0079834 | A1 | * | 4/2007 | Reyes .................... A61B 46/20 128/853 |
| 2009/0211587 | A1 | * | 8/2009 | Lawrentschuk ....... A61B 46/30 128/850 |
| 2011/0030702 | A1 | | 2/2011 | Czajka, Jr. et al. |
| 2011/0146694 | A1 | | 6/2011 | Fischer et al. |
| 2011/0174318 | A1 | | 7/2011 | Reyes et al. |
| 2011/0319844 | A1 | * | 12/2011 | Price ................ B29C 66/24244 604/355 |
| 2012/0017921 | A1 | | 1/2012 | Esquivel et al. |
| 2012/0222686 | A1 | | 9/2012 | Lockwood et al. |
| 2013/0112211 | A1 | * | 5/2013 | Power ................... A61B 46/00 128/853 |

OTHER PUBLICATIONS

Partial International Search Report for Application No. PCT/US2016/057891, dated Jan. 23, 2017, 7 pages.

* cited by examiner

SURGICAL DRAPE WITH ATTACHABLE FLUID CONTROL POUCH AND GEOMETRIC ALIGNMENT FEATURE

BACKGROUND

The present disclosure relates to the field of medical items used during surgery. In particular, the disclosure pertains to an improved drape for covering a portion of a patient's body during a surgery or other medical procedure. More specifically, the subject matter of the present disclosure relates to a surgical drape having a fenestration and an attachable fluid control pouch for receiving bodily fluid and other fluids from a surgical site during a surgical procedure.

Surgical drapes are used during surgery to create a sterile barrier or sterile field around the surgical site, maintain a sterile environment, and reduce the likelihood of infection in the patient and medical staff. Surgical drapes function to prevent bacterial and viral contamination of medical practitioners by the patient, as well as contamination of the patient by non-sterile portions of the patient or by the medical staff and environment during surgery.

Surgical drapes may include one or more fenestrations, or openings, that are designed to provide surgical access to a specific anatomical site of the patient. The fenestration or opening is used to provide access to the surgical site from the sterile field while maintaining a sterile barrier between the surgical site and the remainder of the patient's body and non-sterile portions of the environment. Typically, surgical drapes are fluid repellent or fluid impervious to prevent the passage of fluids, as well as bacterial and viral contaminants, across the sterile barrier. Many modern surgical drapes are made of one or more disposable non-woven fabrics, plastic films, papers, or some combination of these materials.

Some surgical procedures, including many arthroscopic techniques, generate a large volume of fluid as a result of exiting body fluids or irrigation of the surgical site. This fluid could potentially create a slipping hazard if it spills onto the operating room floor. Additionally, uncontrolled fluids could potentially contaminate the sterile field or otherwise compromise the sterile barrier. Thus, the collection, containment and disposal of such fluids is often necessary during the procedure to maintain a clean and safe working environment.

Various methods and devices have been developed to absorb, channel, drain, and collect these fluids during surgical procedures. Absorbent materials such as foams have been attached to the surface of surgical drapes to absorb runoff fluid. However, these absorbent materials can become saturated and leak during procedures involving large volumes of fluid. Thus, bags, pouches, drains, and other devices have been used, with or without absorbent pads, to collect and retain these fluids or drain them away from the surgical site. Presently, many surgical drapes are constructed with a base sheet or panel of non-woven or woven fabric and a smaller sheet or pad of absorbent material that is attached to the base sheet with adhesive. The base sheet and the absorbent pad each have corresponding fenestrations or openings that provide access to the surgical site. The absorbent pad may be backed by a liquid impervious polymer film layer that lies between the absorbent material and the base sheet. The absorbent pad may also serve to reinforce the surgical drape near the surgical site, thus reducing the likelihood of tears or breaches that may compromise the sterile field.

Surgical drapes may include fluid pouches that may be pre-attached to the drape my the manufacturer, or may be attachable by a user near the fenestration to collect runoff fluid from the surgical site. Pre-attachment generally allows the use of bonding tools and techniques that can result in a stronger mechanical connection and/or a leak-proof seal between the pouch and the drape. For example, pre-attached pouches may be heat bonded or sonically bonded to the drape, or may be attached with adhesives such as hot melt glue. On the other hand, user-attachable pouches provide greater flexibility by allowing a user to customize the position and rotational orientation of the pouch on the drape. However, unlike pre-attached drapes which may be sealed to the base sheet underneath upper layers of the drape, user-attachable pouches are generally attached to the drape's absorbent top layer with adhesive such as double-faced tape. The bond between the adhesive and the absorbent top layer cannot typically match the strength and fluid resilience of pre-attached bonds. Moreover, attachment to the top surface, rather than the base sheet, allows runoff fluid to circumvent the pouch by penetrating the between layers at the peripheral edge of the fenestration or by entering the absorbent layer through exposed areas along fluid flow paths between the surgical site and the lip of the pouch.

Surgical drapes are typically designed to be affixed to a patient in an optimal rotational orientation wherein the fluid control pouch is vertically oriented and positioned generally below the surgical site with the pouch opening facing upward to collect fluid flowing from the surgical site under the influence of gravity. In certain circumstances, however, a surgical drape may be affixed to a patient in a non-optimal rotational orientation, either by mistake or intentionally to better accommodate a particular patient anatomy, operating room configuration, or surgeon's preference. In these situations, a pre-attached fluid control pouch may be disposed at an angle that compromises its effectiveness for collecting and retaining fluids. User-attachable pouches may address this problem by allowing the pouch to be attached to the drape in a vertical orientation regardless of the rotational orientation of the drape. However, many surgical drapes have fenestrations or other features that may interfere with optimal pouch placement when the drape is affixed in various rotational orientations.

Thus, there is thus a need in the field of surgical drapes for a drape and a user-attachable fluid control pouch capable of forming an attachment interface with the drape that is stronger, more durable, and has improved barrier qualities. There is also a need for a surgical drape and attachable fluid control pouch that can be reliably attached in an effective or optimal position and orientation for fluid collection regardless of the rotational orientation of the drape.

SUMMARY

Certain aspects of the present disclosure are directed toward a fenestrated surgical drape having an attachable fluid control pouch assembly. The surgical drape and fluid control pouch can have structural features adapted to provide improved fluid flow from a surgical site to the fluid control pouch, thereby reducing the volume of fluid that is spilled or otherwise not collected into the fluid control pouch. The surgical drape and fluid control pouch can provide an improved attachment interface between the pouch and the drape to which it is attached. The attachment interface provides a stronger and more durable adhesive connection between the pouch and the drape and also provides greater resistance to fluid leakage across or through the attachment interface.

In certain aspects, the surgical drape can include a fenestrated base panel, a fenestrated intermediate panel, and a fenestrated mounting panel. The three panels can be aligned with each other so that each of the fenestrations are superimposed in registration with one another, and then can be collectively joined to one another. The intermediate panel can provide a fluid absorbant sheet for absorbing runoff fluids near the surgical site. The mounting panel can provide a top surface capable of achieving a higher quality adhesive bond with the fluid control pouch at the attachment interface than is normally achieved between the fluid control pouch and the surface of the intermediate panel. The mounting panel can have a fluid impervious or fluid repellent top surface to promote fluid flow across the top surface and into the fluid control pouch to reduce the volume of fluid that would otherwise be retained adjacent to the surgical site or channeled away from the fluid control pouch.

In certain aspects, the panels of the surgical drape can be joined together by a continuous seal surrounding the fenestration. In certain aspects, the surgical drape can include improved seal integrity between panels and between panel layers to reduce the occurrence of pathogenic contamination at the surgical site via migration between layers and through the seal. The base sheet and the panels can be aligned so that each of the fenestrations are superimposed in registration with one another, and then can be collectively joined to one another to form a continuous fluid impervious seal surrounding the assembled fenestration. A heat sealing operation can be used to create two or more spaced apart seal locations to provide redundant, higher integrity sealing with greater uniformity throughout the seal.

In certain aspects, the improved seal can provide additional structural integrity to the drape near the attachment location of the fluid control pouch. Specifically, the seal can provide a continuous mechanical bond joining the base panel, the intermediate panel, and the mounting panel, thereby reducing the likelihood of layer separation or delamination due to adhesion degradation in the presence of fluid or under the weight of the attached fluid control pouch, which becomes heavier as the pouch fills with fluid.

In certain aspects, the surgical drape and the fluid control pouch can have corresponding geometric structural features that provide intuitive indication of one or more suggested positions and orientations for attaching the fluid control pouch to the surgical drape. In certain aspects, the fluid control pouch can have an attachment edge, all or a portion of which is contoured to align in registration with all or a portion of the peripheral edge of the surgical drape fenestration in a plurality of rotational orientations relative to the surgical drape. For example, the surgical drape can have a generally circular fenestration, and the fluid control pouch can have a generally U-shaped attachment edge for attaching to the surgical drape. The attachment edge can include a semi-circular arcuate portion that has a slightly larger radius of curvature than the peripheral edge of the drape fenestration. Thus, the arcuate portion of the attachment edge and the peripheral edge of the fenestration can be concentrically aligned at any desired rotational orientation of the fluid control pouch relative to the surgical drape.

In certain aspects, the fluid control pouch can have an attachment edge that has a size, shape, or other geometric structural feature that corresponds to a size, shape, or other geometric structural feature of one or more surgical drape fenestrations associated with the fluid control pouch so as to provide visual indication the fluid control pouch is intended for use with the corresponding drape fenestration(s).

Certain other aspects of the present disclosure are directed toward a methods of making and using a fenestrated surgical drape having an attachable fluid control pouch. In certain aspects, the method can include superimposing a fenestrated base panel, a fenestrated intermediate panel, and a fenestrated mounting panel such that the fenestrations are aligned in registration with each other, and collectively joining the panels together by heat sealing along a peripheral edge surrounding the fenestration to create a continuous fluid impervious seal surrounding the surgical drape fenestration.

In certain other aspects, the method can include rotating the fluid control pouch to any desired one of a plurality of rotational orientations relative to the surgical drape, wherein for each of the plurality of rotational orientations, a geometric feature of the fluid control pouch corresponds to a geometric feature of the surgical drape, and attaching the fluid control pouch to the surgical drape such that the geometric feature of the fluid control pouch for the desired rotational orientation aligns with the corresponding geometric feature of the surgical drape for the desired rotational orientation.

Any feature, structure, or step disclosed herein can be replaced with or combined with any other feature, structure, or step disclosed herein, or omitted. Further, for purposes of summarizing the disclosure, certain aspects, advantages, and features of the devices have been described herein. It is to be understood that not necessarily any or all such advantages are achieved in accordance with any particular embodiments disclosed herein. No individual aspects of this disclosure are essential or indispensable.

BRIEF DESCRIPTION OF THE FIGURES

Embodiments of the present disclosure are described by way of following drawings pointing out the various details of the device and method of the present disclosure. The main features and advantages of the present disclosure will be better understood with the following descriptions, claims, and drawings, where:

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of a surgical drape having an attachable fluid control pouch may be illustrated by describing components that are connected, coupled, attached, bonded and/or joined together. As used herein, the terms "connected", "coupled", "attached", "bonded" and/or "joined" are used interchangeably to indicate either a direct connection between two components or, where appropriate, an indirect connection to one another through intervening or intermediate components.

Relative terms such as "lower" or "bottom", "upper" or "top", and "vertical" or "horizontal" may be used herein to describe one element's relationship to another element illustrated in the drawings. It will be understood that relative terms are intended to encompass different orientations of the surgical drape and fluid control pouch in addition to the orientation depicted in the drawings. By way of example, if aspects of a surgical drape as shown in the drawings are turned over, elements described as being on the "bottom" side of the other element would then be oriented on the "top" side of the other elements as shown in the relevant drawing. The term "bottom" can therefore encompass both an orientation of "bottom" and "top" depending on the particular orientation of the drawing.

Reference will now be made to figures wherein like structures are provided with like reference designations. It should be understood that the figures are diagrammatic and schematic representations of exemplary embodiments of the surgical drape and fluid control pouch of the present disclosure, and are neither limiting nor necessarily drawn to scale.

One exemplary embodiment of the surgical drape of the present disclosure is illustrated in FIGS. 1-4. The surgical drape 100 of this embodiment is particularly suited for arthroscopic shoulder surgery performed with the patient in the so-called "beach chair" or Fowler's position. In the beach chair position the patient is seated upright and somewhat reclined, which results in a position similar to a position of a person sitting in a beach chair. The surgical drape 100 can be used for surgery on either the left or the right shoulder.

Figure 1:
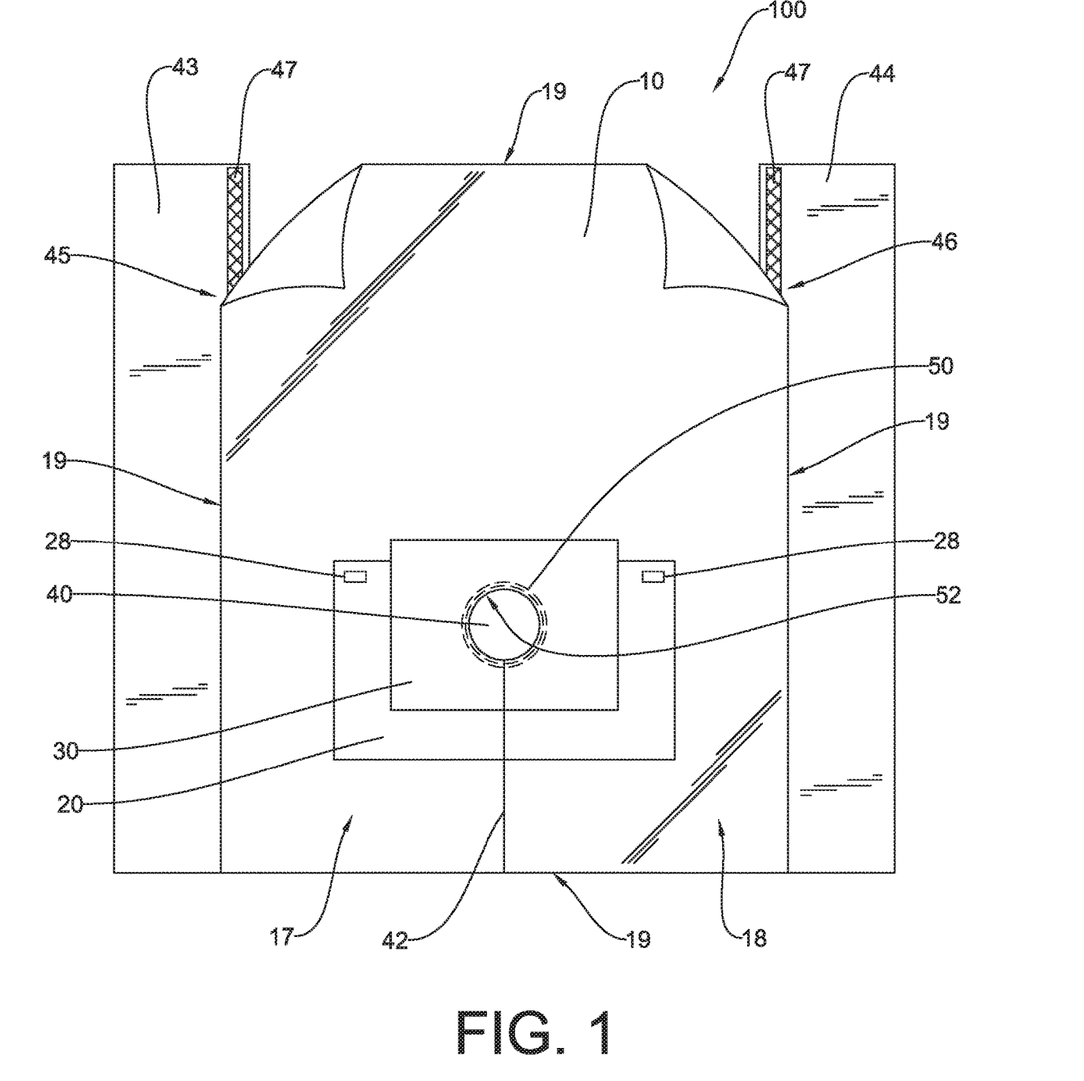
FIG. 1 is a top view of a first embodiment of the surgical drape according to certain aspects of the present disclosure.

As illustrated in FIG. 1, the surgical drape 100 defines a fenestration 40 and includes a base panel 10, an intermediate panel 20, and a mounting panel 30. The surgical drape 100 is flexible such that the peripheral edge 52 circumscribing the fenestration 40 can be sealed to the patient and expose any desired area of the shoulder for surgery. A slit 42 extends from the fenestration 40 to an outer peripheral edge 19 of the drape 100 and defines opposing left and right sides 17, 18 of the drape 100. The slit 42 provides access to the fenestration 40 and allows portions of the left and right sides 17, 18 to overlap so that the drape 100 may be wrapped tightly around the patient and conform more closely to the patient's body.

Figure 2:
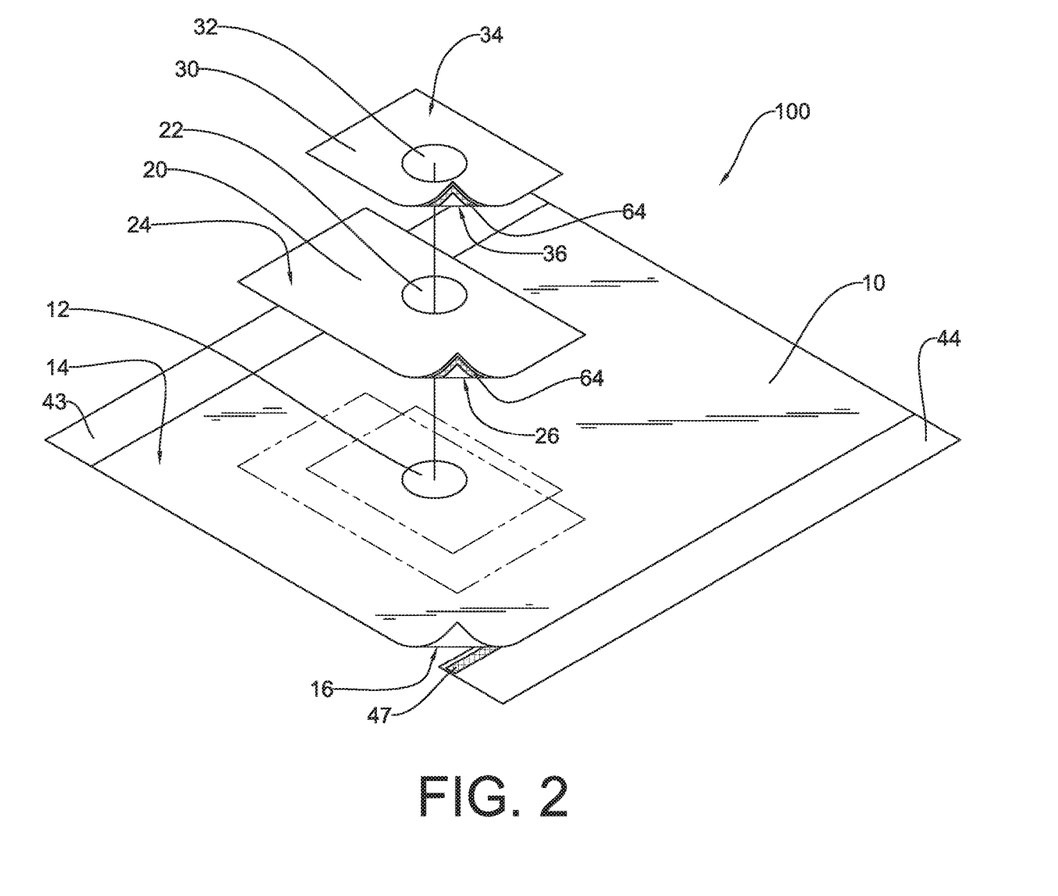
FIG. 2 is an exploded isometric view of the surgical drape of FIG. 1.

The surgical drape 100 is arranged such that the intermediate panel 20 is layered on the top surface 14 of the base panel 10, and the mounting panel 30 is layered on the top surface 24 of the intermediate panel 20. The panels 10, 20, 30 are superimposed such that corresponding fenestrations 12, 22, 32 are aligned in registration with each other, as illustrated in FIG. 2. The panels 10, 20, 30 are joined together by a continuous fluid impervious seal 50 that circumscribes the fenestration 40.

The base panel 10 is a large flexible sheet of material, generally rectangular in the shown embodiment but it can be any suitable shape, provided it is large enough to cover a human body or a sufficient portion of the body adjacent the surgical site to assist in providing a sterile field at the surgical site. The base panel 10 defines a fenestration 40 generally in a central region near the center portion of the base panel 10, however, it could be located off-center near any peripheral edge 19 of the base panel 10. Optional base panel extensions 43, 44 may be attached to the base panel 10 by glue 47 or by heat seal or other suitable means, and preferably seams 45, 46 are sealed to prevent passage of fluid and contaminants between base panel 10 and base panel extensions 43, 44.

The base panel 10 and base panel extensions 43, 44 can be made of any of a variety of suitable commercially available medical fabric materials. Typically, the base panel material is fluid impervious. Such medical fabric materials known in the surgical field include without limitation non-woven fabrics. "Non-woven fabrics" as used herein refers to a single web, or an assembly or laminate of multiple webs, formed of individual randomly laid fibers, for example using a spunlaid, thermobonded, spunbonded, meltblown or bonded carded web process. A laminate of non-woven fabrics is one conventional material in the surgical field that could be used for the base panel 10. In several embodiments, including the embodiment illustrated in FIG. 4, one example of a suitable medical fabric material for the base panel 10 is a combination spunbonded/meltblown/spunbonded laminate of polypropylene fibers commonly referred to as SMS. Another example of a suitable medical fabric material for the base panel is a combination non-woven fabric and film in which a liquid impervious polymer film is disposed between two non-woven layers.

In any of these composite sheet materials, the individual web layers can be joined together throughout some or all of the surface area and/or along the periphery using any suitable mechanical, thermal, or chemical bonding process, such as point or pattern bonding by the application of heat and/or pressure to the webs. The fibers comprising the various webs can be hydrophilic (liquid absorbing) or hydrophobic (liquid repelling) depending on the material selected. Particularly when a liquid impervious layer is used, such as an inner polymer film, the outer facing layer can be made of hydrophilic fibers, or treated with a surfactant to be absorbent. Particularly when a liquid impervious layer is not used in the make up of the base panel 10, the exposed outer layer of the base panel 10 may made of hydrophobic fibers, or may be treated to be liquid repellent, so that blood or other body fluids present during surgery do not absorb into the base panel 10 and migrate through the material into contact with the patient's body.

The base panel 10 can be constructed of outer webs of different colors or indicia, or a single web with different colors or indicia on each side, to provide visual indication of the difference in material or surface treatments between the sides of the drape. This would help the practitioner identify the proper side to face the patient, for example, if a softer or hydrophobic web was used at the underside of the base panel.

Referring again to FIGS. 1 and 2, the intermediate panel 20 has a smaller surface area than the base panel 10 and defines an intermediate panel fenestration 22 generally in a central region of the intermediate panel 20. The intermediate panel fenestration 22 has a similar size and shape as the base panel fenestration 12.

The intermediate panel 20 may be made from a variety of suitable materials. One preferred material is a laminate of open-celled foam backed by fluid repellent or fluid impervious film. Another suitable material is a spunbonded web of hydrophilic fibers or fibers having a surface treatment to be absorbent, and can have a fluid repellent or fluid impervious sealable component, preferably in the form of a polymer film layer at the underside of the non-woven fabric layer, which is compatible for bonding with the top side of the base panel. In several embodiments, including the embodiment illustrated in FIG. 4, the intermediate panel 20 is a spunbond/meltblown/film (SMF) laminate composed of polypropylene spunbond and meltblown nonwoven layers and a polyethylene-polypropylene copolymer film. Laminate layers may be ultrasonically bonded or bonded with adhesive, heat and/or pressure. One or more layers may be treated with wetting agents to provide a wettable and absorbent structure.

The mounting panel 30 typically has a smaller surface area than the intermediate panel 20 and defines a mounting panel fenestration 32 generally in a central region of the mounting panel 30. The mounting panel fenestration 32 has a similar size and shape as the base panel fenestration 12. It should be appreciated that the mounting panel 30 can be contained entirely within the perimeter of the intermediate panel 20, or alternatively one or more portions of the mounting panel 30 may extend beyond the perimeter of the intermediate panel 20 and thus overly the base panel 10, as shown in FIG. 1.

The mounting panel 30 may be made from a variety of suitable materials. Suitable materials preferably have a top surface that is either inherently fluid repellent or fluid impervious, or is treated to be fluid repellent or fluid impervious. Preferably, the mounting panel top surface 34 is made from a material capable of forming strong, fluid resistant bonds with adhesives. Preferably, underside surface 36 of the mounting panel 30 is chemically compatible with top surface 24 of the intermediate panel 20 such that a strong, fluid resistant bond can be formed between the mounting panel 30 and the intermediate panel 20. In several embodiments, including the embodiment illustrated in FIG. 4, a suitable mounting panel material is an SMS/film laminate having an underside surface layer of SMS and a top surface layer of polymer film.

Figure 3:
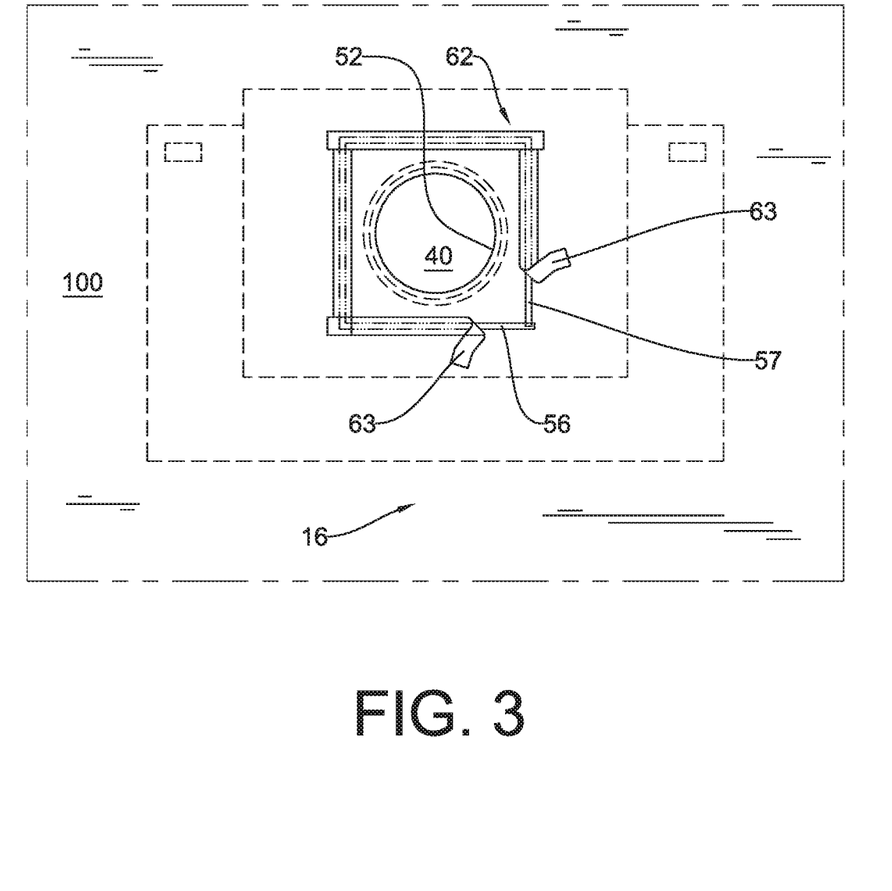
FIG. 3 is a detail view of the fenestration area of the surgical drape of FIG. 1, shown from below.

The surgical drape 100 may include various areas that have an adhesive for attaching the areas to a desired location. For example, adhesive strips or adhesive tape 62 may be attached to underside surface 16 of the drape 100 along the peripheral edge 52 surrounding the fenestration 40. The adhesive 62 has a cover or liner 63 that is removed to expose the adhesive, which can then be adhered to another part of the drape, the patient or any other desired location. Preferably, as illustrated in FIG. 3, individual tape segments 56, 57 are overlapped to provide a continuous band of adhesive surrounding the fenestration 40 so that the surgical drape 100 can be sealed to the patient around the surgical site when the patient's shoulder extends through the fenestration 40. It will be appreciated that adhesive tape or other appropriate adhesive can be applied to various other portions of the surgical drape 100. The adhesive surrounding the fenestration can be an adhesive suitable for prolonged contact with the patient's skin for the duration of the procedure. Additionally, one or more straps 28, clips, ties, hooks, or other retention devices may be attached to the drape 100 in any location to assist with routing surgical instrument cords and keeping equipment away from the surgical site, or to hold equipment and supplies for easy access near the surgical site.

In certain aspects, the surgical drape 100 may include an elastomeric panel occluding all or a portion of the fenestration 40. The height and width of the elastomeric sheet may be such that the outer perimeter of the elastomeric sheet extends beyond the peripheral edge 52 surrounding the fenestration 40. The elastomeric sheet may be disposed between the base panel 10 and the intermediate panel 20, or between the intermediate panel 20 and the mounting panel 30. The elastomeric sheet may be joined together with the individual panels by the seal 50. Alternatively, the elastomeric sheet may be attached to the base panel bottom surface 16 or the mounting panel top surface 34. The elastomeric panel may include one or more sealing layers to improve chemical compatibility with adjacent layers and increase the bond strength of the seal 50, as described in greater detail below. The elastomeric sheet may contain an aperture, smaller in size than the fenestration 40, adapted to accommodate insertion of a patient's arm or other extremity when inserted therethrough. The contoured opening may be adapted to accommodate the natural geometry of the shoulder anatomy and create a circumferential seal that completely surrounds the patient's shoulder or other extremity. The slit 42 would preferable be omitted in drapes that include such apertured elastomeric panels.

An important aspect of the surgical drape 100 of the present disclosure is the seal 50 that joins the drape panels 10, 20, 30 near the peripheral edge 52 of the fenestration 40. Several features of the seal 50 and sealing technique serve to improve the integrity and strength of the seal 50 and thereby improve its effectiveness as a barrier to contaminants. Briefly, these features include the non-linear, continuous configuration of the seal, the use of multiple, narrow seal regions circumscribing the aperture and fenestration and the use of a heat sealing technique to join the panels with the application of heat and pressure. Additionally, it is preferable that panels 10, 20, 30 are made of materials that are chemically compatible such that they can form strong, fluid impervious bonds when joined together by adhesive, heat, pressure, or a combination thereof.

Figure 4:
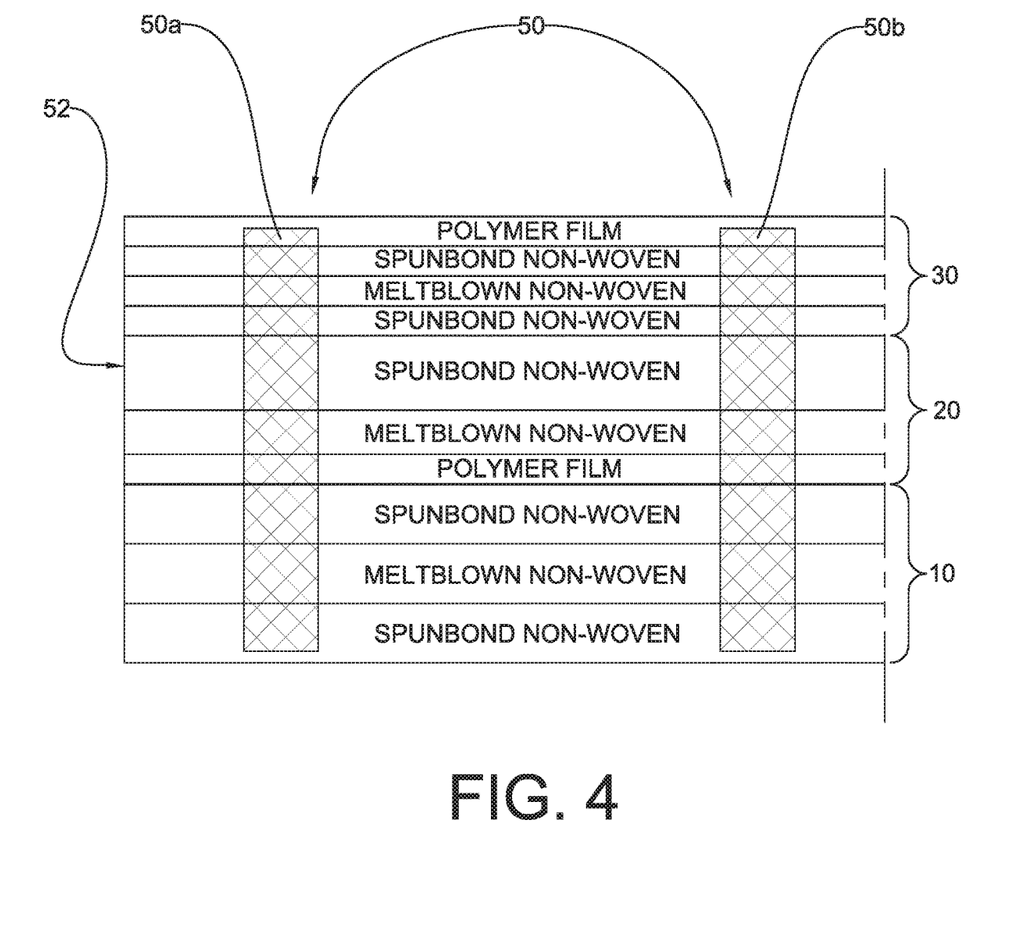
FIG. 4 is an enlarged cross-section view of the peripheral edge of the fenestration and seal area of the surgical drape of FIG. 1, shown from the side.

More specifically, one preferred embodiment of the seal 50 is illustrated in FIG. 4. In this embodiment the seal 50 is formed by two distinct concentric circular regions 50a, 50b circumscribing the surgical drape fenestration 40. The two seal regions 50a, 50b are spaced apart, with the inner seal region 50a being spaced a radial distance from the peripheral edge 52 of the fenestration 40, and the outer seal region 50b being spaced a radial distance from the inner seal region 50a.

The seal 50 thus joins all three panels 10, 20, 30 with a liquid impervious thermally and mechanically bonded seal surrounding the fenestration 40. The seal prevents fluid penetration between layers at the peripheral edge of fenestration and "channeling" or seepage of fluid through or between panel layers to areas spaced radially outward from the seal, and vice-versa.

Another feature of the seal 50 that improves its barrier effectiveness is that a redundant seal is established by virtue of having two distinct seal regions 50a, 50b. Since each seal region 50a, 50b surrounds the fenestration 40 entirely, each independently works to provide a barrier. If any portion of the inner seal region 50a were to fail, the outer seal region 50b could provide barrier resistance and vice-versa. Moreover, by using two narrow seal regions, for example two ¼ inch thick seal regions instead of one ½ inch thick seal region, and spacing them apart, the total seal bonding area is increased, by virtue of the larger diameter of the outer seal region 50b caused by spacing the outer seal region 50b radially outward.

To summarize, the seal has more uniform bonding throughout the seal regions in the short radial dimensions. The uniformity of the bonding in the long circular dimensions of the seal regions is improved as well due to the non-linear configuration eliminates hot spots. Further, built-in redundancy of the two seal regions improves the overall integrity of the seal should bonding of one of the regions become compromised. And, the overall bond area is increased. The result is a liquid impervious seal with improved barrier properties to contaminants.

The seal 50 is formed by thermally and mechanically bonding the panels 10, 20, 30 together with heat and pressure using a heat sealing operation. Prior to the heat sealing operation, the panels 10, 20, 30 are formed by manual or automated processes, for example, by separately unwinding spools of web material and then forming the fenestrations 12, 22, 32 by independent roll, die or other cutting operations. The webs are cut to define individual panels of the desired size and shape. The panels are brought together in the proper order and orientation as described herein. The fenestrations are superimposed in registration with each other and the panels are joined by forming the aforementioned heat seal about the fenestration. A suitable heat sealing machine, such as that manufactured by Therm-O-Seal, of Mansfield, Tex., can be used. In one preferred process, the seal is formed by applying pressure in the range of about 60-80 psi at 200-350° F. for a cycle time of between about 4-5 seconds.

In addition to the seal 50 surrounding the drape fenestration 40, a suitable bonding agent or technique can be used to affix other portions of the intermediate panel 20 to the base panel 10, and other portions of the mounting panel 30 to the intermediate panel 20 and/or the base panel 10. Such a bonding agent can be a double-sided tape or a liquid adhesive, such as a hot melt glue, that is chemically compatible with both of the mating materials. The adhesive can be applied to the entire mating surface or to any portion thereof. In one preferred form, a liquid adhesive is applied to adhesive areas 64 in the margin of the perimeter along the underside 26 of the intermediate panel 20 and along the underside 36 of the mounting panel 30 near its perimeter, as illustrated in FIG. 2. The adhesive could be replaced by another bonding technique, such as ultrasonic welding.

Another advantage of the seal 50, in addition to improved barrier effectiveness and seal integrity, is that the seal 50 provides improved structural integrity of the drape near the attachment location of the fluid control pouch 70. Specifically, the seal 50 can provide a continuous mechanical bond between the base panel 10 and the mounting panel 30, thereby reducing the likelihood of layer separation or delamination due to adhesion degradation in the presence of fluid or under the weight of the pouch 70, which typically becomes heavier as the pouch fills with fluid.

Figure 5:
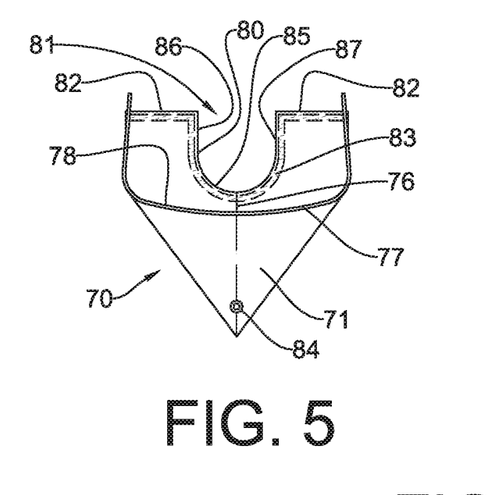
FIG. 5 is a top view of a first embodiment of the attachable fluid control pouch according to certain aspects of the present disclosure.
Figure 6:
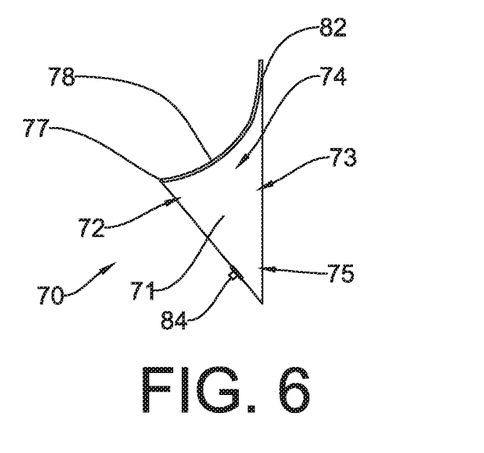
FIG. 6 is a side view of the fluid control pouch of FIG. 5.

It will be appreciated by those skilled in the art that a variety of suitable fluid control pouches may be adapted for use in conjunction with the surgical drape described herein. One example embodiment of a suitable fluid control pouch usable with the surgical drape 100 of the embodiment of FIGS. 1-4 is illustrated in FIGS. 5-6 in a vertically upright orientation. The pouch 70 comprises a single folded sheet 71 of flexible fluid impermeable material, and has a front distal portion 72 and a rear proximal portion 73 relative to the patient's body. The pouch 70 also includes an upper portion 74 and a lower portion 75 The flexible sheet 71 is composed of a single contiguous sheet having a generally conical configuration with the ends of the flexible sheet connected in a fluid impervious seal 76 along the rear portion 73. In one embodiment, the pouch is comprised of a polymer. In another embodiment, the pouch is comprised of polyethylene.

A drawstring 77 is provided at an upper pouch edge 78. The drawstring 77 is formed from a malleable and form retentive material such that the pouch can be held up and out, and shaped as needed to enhance fluid collection and/or access to the surgical site. In one embodiment, the drawstring is a wire. Optionally, the fluid control pouch 70 can include one or more conformable strips (not shown) that can be shaped to provide additional customization of the shape of the fluid control pouch 70. In one embodiment these additional strips are also wires. In another embodiment, the conformable strips are added inside the pouch. In a further embodiment, the conformable strips are inside the pouch, on the front distal portion 72.

The lower portion 75 of the pouch 70 includes a drainage port 84, which is closed prior to use. The drainage port 84 is opened to define fluid flow paths from inside the pouch to outside the pouch and drain fluids collected in the pouch during the medical procedure. The drainage port 84 can be beveled or shielded to reduce or prevent clogging by surgical debris. It should be appreciated that the fluid control pouch can be provided with any desired configuration including or one or more valves, ports, connectors, or other openings for draining, evacuating, sampling fluid, or otherwise handling fluid collected in the pouch.

The fluid control pouch 70 includes an attachment edge 80 that defines a generally U-shaped slot 81 recessed from upper edge 82 of the rear portion 73 of the pouch 70. The attachment edge 80 includes an arcuate portion 85 and opposing parallel portions 86, 87 extending from opposite ends of the arcuate portion 85 to the upper edge 82 of the rear portion 73 of the pouch 70. Adhesive strips or adhesive tape 83 is attached to the outside proximal surface 79 of the flexible sheet 71 along the attachment edge 80 and the upper edge 82 of the rear portion 73. The adhesive 83 is provided with a cover or liner (not shown) that is removable to expose the adhesive, which can then be adhered the surgical drape 100 to secure the fluid control pouch 70 to the surgical drape 100. Preferably, the adhesive 83 comprises either a continuous strip or individual segments that are overlapped to provide a continuous strip of adhesive along the attachment edge 80 and the upper edge 82 of the rear portion 73.

Figure 7:
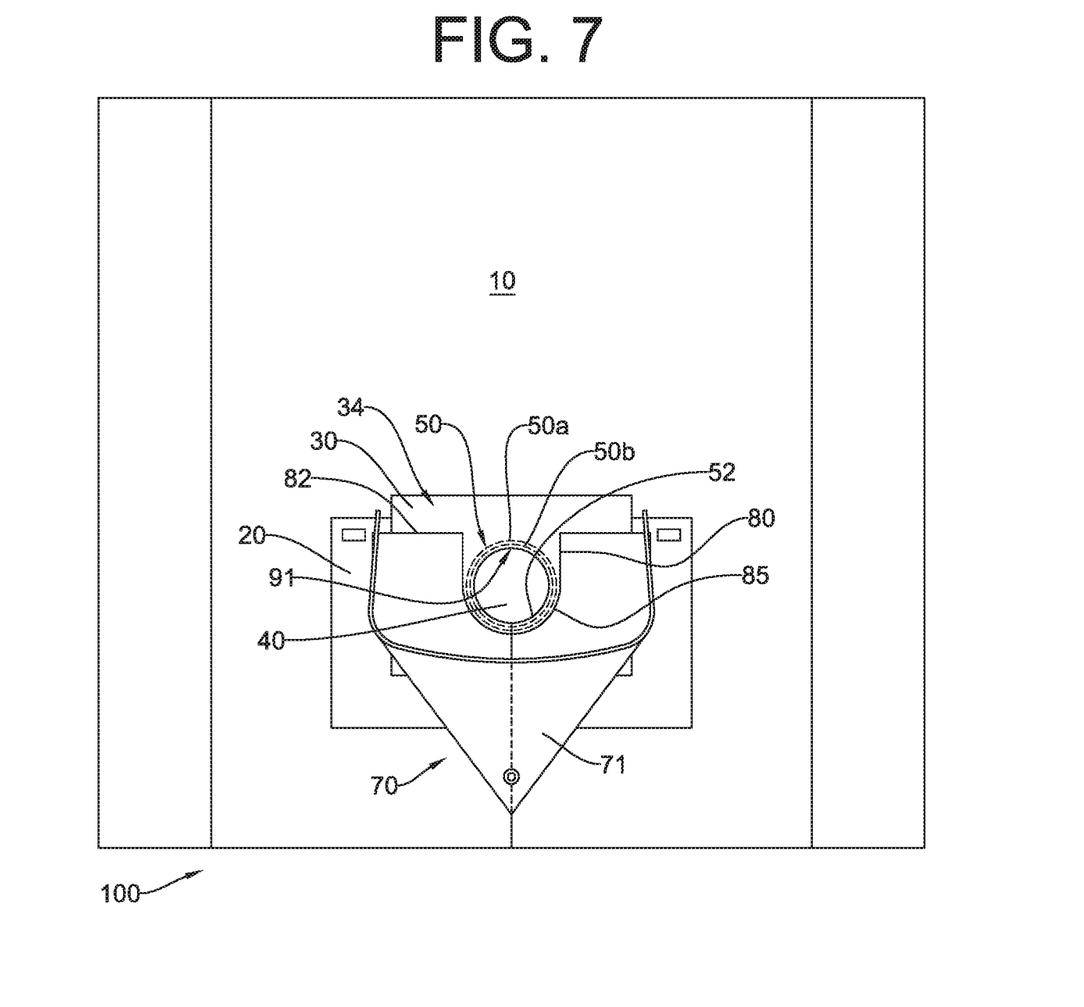
FIG. 7 is a top view of the surgical drape of FIG. 1 and the fluid control pouch of FIG. 5 shown in an attached position.
Figure 8:
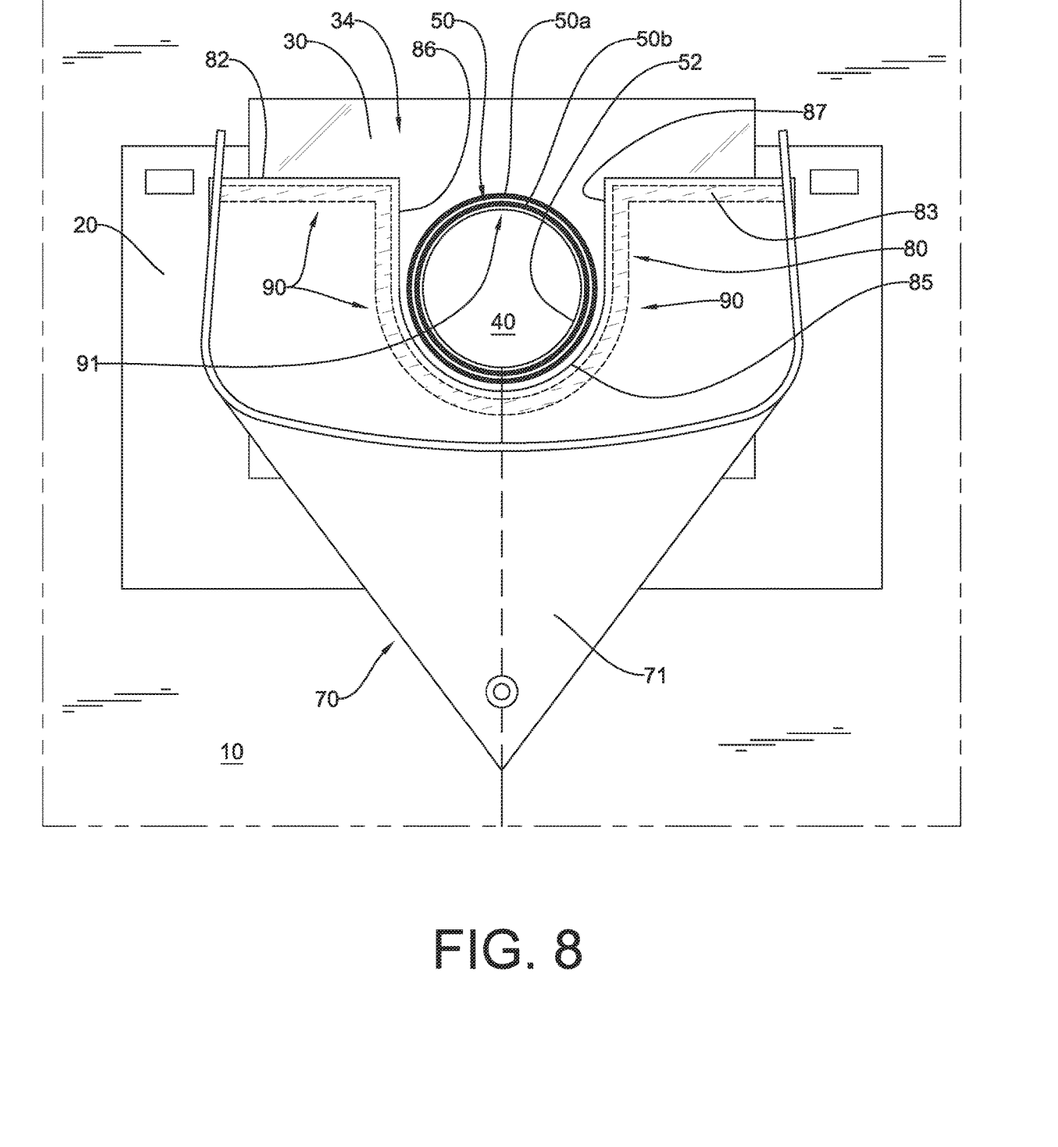
FIG. 8 is a detail view of the fluid control pouch of FIG. 5 shown attached to the surgical drape of FIG. 1.

Referring to FIGS. 7 and 8, the fluid control pouch 70 is shown attached to the surgical drape 100 such that the arcuate portion 85 of the attachment edge 80 of the pouch 70 is concentrically aligned with the peripheral edge 52 of the drape fenestration 40. Preferably, the arcuate portion 85 is spaced radially outward from the outer seal region 50b so that any dimensional variation in the mounting panel top surface 34 at the seal 50 does not interfere with the attachment interface 90 between the pouch 70 and the drape 100. The opposing parallel portions 86, 87 of the attachment edge 80 extend upward beyond the uppermost portion 91 of the peripheral edge 52 of the fenestration 40. Thus, the fenestration is effectively positioned entirely within the U-shaped slot 81 defined by the attachment edge 80, such that the attachment edge 80 substantially surrounds the fenestration 40 to facilitate the flow of fluid from the surgical site into the pouch and minimize fluid leakage around the sides of the pouch.

When the fluid control pouch 70 is attached to the surgical drape 100, the attachment edge 80 and at least a portion of the upper edge 82 of the rear portion 73 of the pouch 70 are secured to the mounting panel top surface 34 via the adhesive 83. The mounting panel top surface 34 is capable of achieving a higher quality adhesive bond with the fluid control pouch adhesive 83 than would normally be achieved between the adhesive and an absorbent surface, such as, for example, the spunbond non-woven top surface 24 of the intermediate panel 20. The higher quality adhesive bond provides greater resistance to the passage of fluid and contaminants across the attachment interface. Additionally, the top surface 34 of the mounting panel 30 cooperates with the seal 50 surrounding the fenestration 40 to provide a continuous, fluid impervious and/or fluid repellent, and non-absorbent fluid flow path between the surgical site and the fluid control pouch 70. This arrangement reduces or eliminates the entry and channeling of fluid between layers at the peripheral edge 52 of the fenestration 40 that can occur with surgical drapes having layers that are not sealed or are inadequately sealed together surrounding the fenestration. Similarly, the present surgical drape 100 separates absorbent drape layers from primary fluid flow paths to prevent leakage that could result from fluid channeling through or saturating absorbent drape layers. Thus, the improved seal 50 joining the panels of the surgical drape 100 around the fenestration 40, as well as the improved attachment interface 90 between the mounting panel 30 and the fluid control pouch 70, are configured to prevent fluid from circumventing the fluid control pouch 70. Furthermore, these improved features reduce the likelihood of drape layer separation and adhesive degradation due to fluid attack and/or mechanical stresses that could cause detachment of the fluid control pouch or could otherwise compromise its ability to collect and retain runoff fluid.

In several embodiments, the surgical drape and the attachable fluid control pouch include corresponding geometric structural features that provide intuitive indication of one or more suggested positions and orientations for attaching the fluid control pouch to the surgical drape. Referring to FIG. 8, the surgical drape 100 of this illustrated example embodiment has a generally circular fenestration 40. The U-shaped attachment edge 80 of the fluid control pouch 70 includes a semi-circular arcuate portion 85 that preferably has a slightly greater radius of curvature than the peripheral edge 52 of the drape fenestration 40. When these arcuate features 85, 52 are placed in concentric alignment, the attachment edge 80 substantially surrounds the fenestration 40, thereby positioning the pouch opening adjacent to the surgical site.

Figure 9:
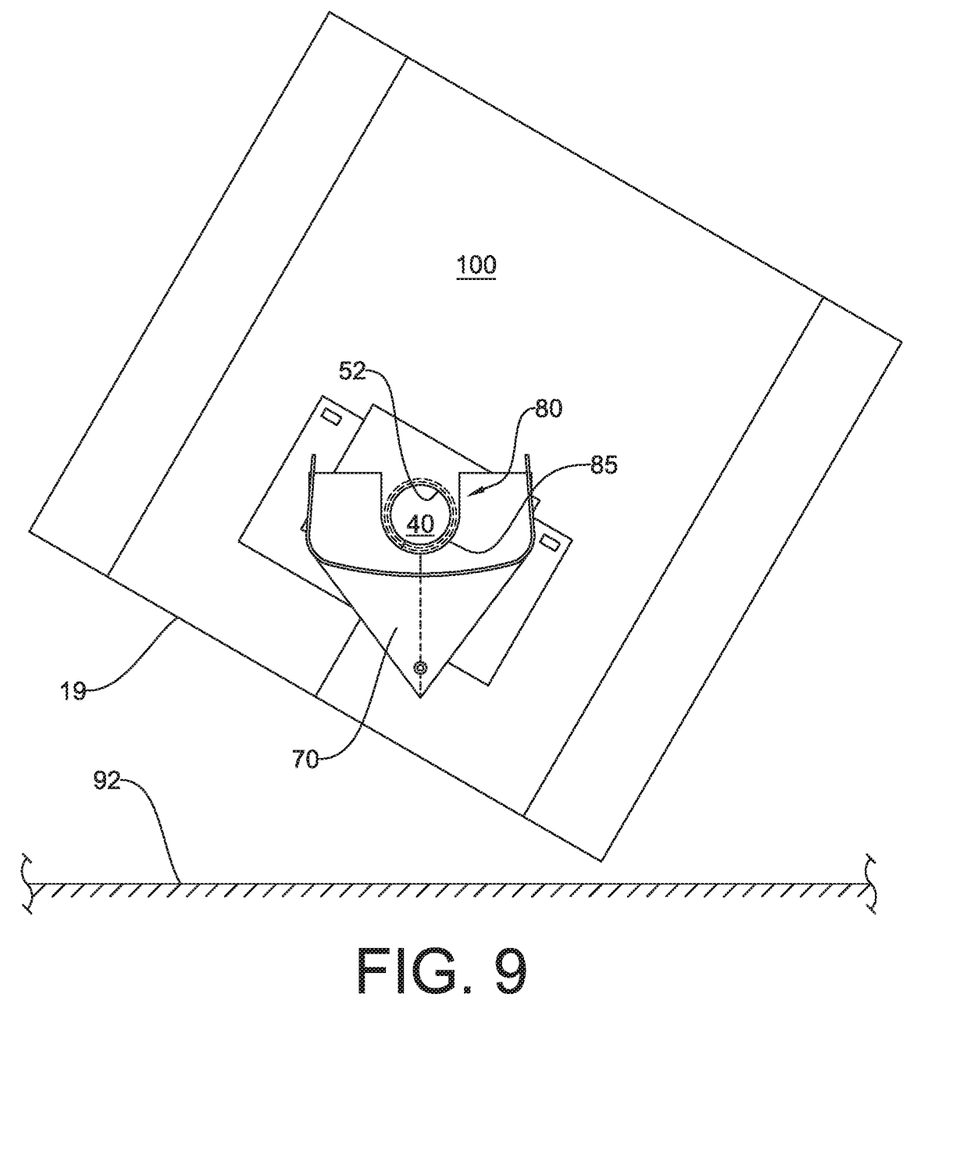
FIG. 9 illustrates the surgical drape of FIG. 1, oriented such that its bottom edge is not parallel to an operating room floor, and the fluid control pouch of FIG. 5, shown in a vertical orientation relative to the operating room floor.

As exemplified in FIG. 9, even if the surgical drape 100 is attached to the patient such that it's bottom peripheral edge 19 is not horizontal (i.e., parallel to the operating room floor 92), the fluid control pouch 70 can be oriented vertically upright and positioned to provide effective fluid collection by bringing the arcuate portion 85 of the attachment edge 80 into concentric alignment with the circular peripheral edge 52 of the fenestration 40. Thus the arcuate portion 85 of the attachment edge 80 and the peripheral edge 52 of the fenestration 40 are corresponding geometric features that can function as indicia for positioning the fluid control pouch 70 effectively regardless of its rotational orientation relative to the drape 100.

Figure 10:
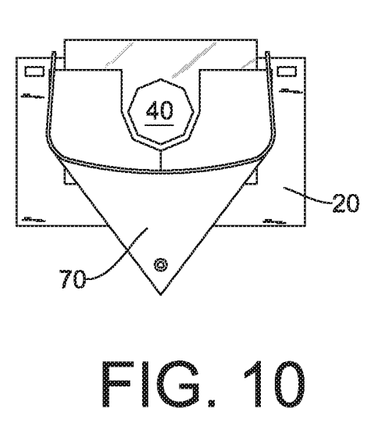
FIG. 10 illustrates a portion of a surgical drape and an attached fluid control pouch shown in vertical rotational alignment with each other, in accordance with certain other aspects of the present disclosure.
Figure 11:
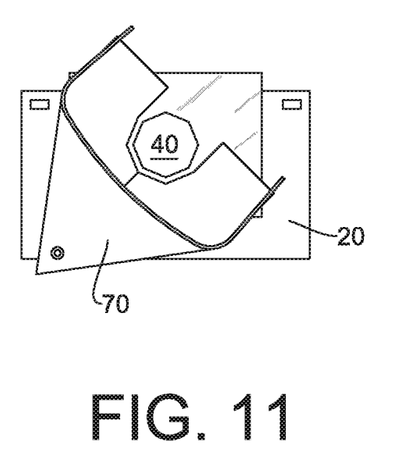
FIG. 11 illustrates the portion of the surgical drape and the attached fluid control pouch of FIG. 10, shown with the fluid control pouch in a rotated orientation relative to the surgical drape.
Figure 12:
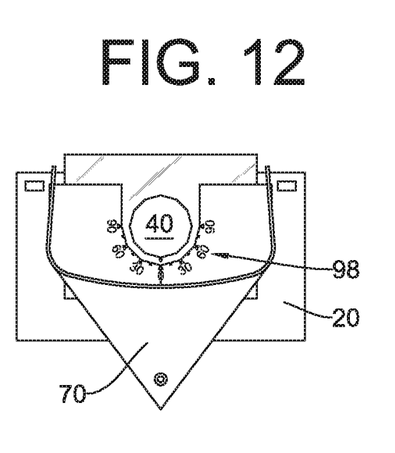
FIG. 12 illustrates a portion of a surgical drape and an attached fluid control pouch shown in vertical rotational alignment with each other, in accordance with certain other aspects of the present disclosure.
Figure 13:
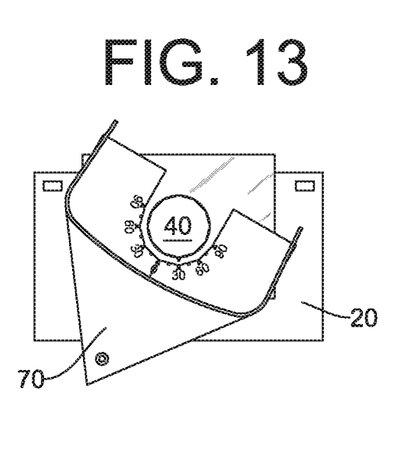
FIG. 13 illustrates the portion of the surgical drape and the attached fluid control pouch of FIG. 12, shown with the fluid control pouch in a rotated orientation relative to the surgical drape.

It should be appreciated that a variety of suitable geometric features can be incorporated into the attachment edge and fenestration to provide indication of various relative positions and orientations. In certain embodiments, as illustrated in FIGS. 10 and 11 equilateral polygonal segments can be substituted for circular segments to indicate both suggested positions as well as incremental rotational orientations of the pouch relative to the drape. In certain embodiments, the attachment edge and fenestration are provided with corresponding but different geometric features. For example, in several embodiments, the fenestration is circular while the attachment edge includes equilateral polygonal segments that circumscribe the fenestration. In several embodiments, the pouch and/or the drape can include other visual indicia, such as printed symbols for indicating one or more positions and/or orientations. Optionally, the other visual indicia can cooperate with structural features of the pouch or the drape for indicating one or more positions and/or orientations, as illustrated in the example embodiment of FIGS. 12 and 13.

The general method for using a surgical drape in accordance with certain aspects of the present disclosure is as follows. To place the pouch and drape onto a patient in preparation for surgery, the patient is positioned into the "beach chair" or Fowler's position. The pouch 70 and the drape 100 are unpackaged and unfolded to provide access to the fenestration 40 and the adhesive portion 62 on the underside 16 of the base panel 10. The adhesive surface of the adhesive portion 62 is exposed. The patient's arm is directed through the fenestration 40 as the drape is pulled onto the patient such that the fenestration 40 circumscribes the area above the shoulder, and the adhesive portion 62 is adhered to the patient to form a seal surrounding the surgical site. If the drape includes an elastomeric panel, the elastomeric panel may form a seal around the patient's shoulder extremity near or adjacent to the surgical site. At this point, the remainder of the drape 100 can be released and unfolded. The adhesive 83 at the attachment edge 80 is exposed and the pouch 70 is rotated to a desired rotational orientation relative to the drape 100. The pouch 70 is positioned such that the arcuate portion 85 of the attachment edge 80 is in concentric alignment with the corresponding segment of the peripheral edge 52 of the fenestration, and the pouch is adhered at least to the mounting panel top surface 34.

The foregoing description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

The invention claimed is:

1. A surgical drape and fluid collection device comprising:
   a surgical drape comprising:
   a base panel defining a base panel fenestration;

an intermediate panel comprising a fluid absorbent material, defining an intermediate panel fenestration, and having a surface area smaller than that of the base panel; and a mounting panel having a fluid impervious top surface, defining a mounting panel fenestration, and having a surface area smaller than that of the intermediate panel, the intermediate panel being disposed between the base panel and the mounting panel, wherein the base panel fenestration, the intermediate panel fenestration, and the mounting panel fenestration are congruent and superimposed in registration with each other and collectively joined together by a continuous fluid impervious seal surrounding the drape fenestration, wherein the fluid impervious seal is configured to prevent fluid penetration between the base panel, intermediate panel, and mounting panel at edges of the mounting panel fenestration; and a fluid collection device configured to be selectively mounted to the mounting panel, wherein the top surface of the mounting panel is configured to receive the fluid collection device having an attachment edge including an arcuate portion, the mounting panel and the fluid collection device including geometric structural features for attaching the fluid collection device to the top surface of the mounting panel, wherein the fluid collection device is selectively mounted to substantially surround the seal by a user, at least a portion of the attachment edge being optionally alignable with either:

(i) a corresponding first portion of a peripheral edge of the drape fenestration when the fluid collection device is in a first rotational orientation relative to the surgical drape; and (ii) a corresponding second portion of the peripheral edge of the drape fenestration when the fluid collection device is in a second, different rotational orientation relative to the surgical drape.

2. The surgical drape of claim 1, wherein the base panel, the intermediate panel, and mounting panel are joined together by at least two distinct seal regions.

3. The surgical drape of claim 2, wherein each of the seal regions surrounds the fenestration via a continuous, closed seal path.

4. The surgical drape of claim 1, wherein the seal joining the base panel, the intermediate panel, and the mounting panel is formed by heat and pressure.

5. The surgical drape of claim 1, wherein the fluid collection device is attachable to the top surface of the mounting panel via adhesive such that adhesive interfaces between the top surface of the mounting panel and the fluid collection device are fluid impervious and resistant to adhesive degradation due to contact with runoff surgical waste fluid.

6. The surgical drape of claim 5, wherein the mounting panel surrounds the drape fenestration to provide a continuous, fluid impervious and non-absorbent flow path between a peripheral edge of the drape fenestration and the fluid collection device.

7. A surgical drape and fluid collection combination device comprising: a surgical drape comprising:

a base panel defining a base panel fenestration;
an intermediate panel comprising a fluid absorbent material and defining an intermediate panel fenestration; and
a mounting panel having a fluid impervious top surface and defining a mounting panel fenestration, the intermediate panel being disposed between the base panel and the mounting panel,
the base panel fenestration, the intermediate panel fenestration, and the mounting panel fenestration are congruent and superimposed in registration with each other and collectively joined together by a continuous fluid impervious seal surrounding the drape fenestration, wherein the fluid impervious seal is configured to prevent fluid penetration between the base panel, intermediate panel, and mounting panel, at edges of the mounting panel fenestration; and
a fluid collection device having an attachment edge that includes an arcuate portion, the fluid collection device being configured to be selectively attachable to the mounting panel in either a first rotational orientation with respect to the mounting panel or a second rotational orientation different from the first rotational orientation with respect to the mounting panel, the mounting panel and the fluid collection device including geometric structural features for attaching the fluid collection device to the top surface of the mounting panel, wherein the fluid collection device is selectively attached substantially surrounding the seal by a user, the fluid collection device comprising:
a single folded sheet;
the fluid collection device having a front distal portion and a rear proximal portion; and
an upper portion and a lower portion,
the single folded sheet being composed of a single contiguous sheet having a conical configuration with ends of the sheet connected in a fluid impervious seal along the rear portion.

8. The surgical drape and fluid collection combination device of claim 7, wherein the fluid collection device is a pouch.

9. The surgical drape and fluid collection combination device of claim 8, wherein a drawstring is provided at an upper pouch edge.

10. The surgical drape and fluid collection combination device of claim 8, wherein the pouch includes a drainage port.

11. The surgical drape and fluid collection combination device of claim 8, wherein the attachment edge of the pouch has a u-shape recessed from an upper edge of the rear portion of the pouch.

12. The surgical drape and fluid collection combination device of claim 8, wherein the arcuate portion of the pouch is concentrically aligned with a peripheral edge of the drape fenestration.

13. The surgical drape and fluid collection combination device of claim 12, wherein the arcuate portion is spaced radially outward from an outer seal region so that any dimensional variation in the top surface of the mounting panel at the seal does not interfere with an attachment interface between the pouch and the drape.

14. The surgical drape and fluid collection combination device of claim 7, wherein the fluid collection device is selectively attachable to the top surface of the mounting panel via adhesive such that adhesive interfaces between the top surface of the mounting panel and the fluid collection device are fluid impervious and resistant to adhesive degradation due to contact with a runoff surgical waste fluid.

15. The surgical drape and fluid collection combination device of claim 14, wherein the mounting panel surrounds the drape fenestration to provide a continuous, fluid impervious and non-absorbent flow path between a peripheral edge of the drape fenestration and the fluid collection device.

16. A surgical drape with a drape fenestration comprising:
a base panel defining a base panel fenestration;
an intermediate panel comprising a fluid absorbent material, defining an intermediate panel fenestration;
a mounting panel having a fluid impervious top surface and defining a mounting panel fenestration, wherein the intermediate panel is disposed between the base panel and the mounting panel, and wherein the base panel fenestration, the intermediate panel fenestration, and the mounting panel fenestration are substantially the same diameter and are superimposed so as to be in registration with each other and collectively joined at a continuous fluid impervious seal configured to prevent fluid penetration between the base panel, intermediate panel, and mounting panel, and surrounding the base panel fenestration, the intermediate panel fenestration and the mounting panel fenestration so that the superimposed fenestrations of the base panel, the intermediate panel, and the mounting panel collectively define the drape fenestration; and
a fluid collection device having an attachment edge that includes an arcuate portion, the fluid collection device being configured to be selectively attachable to the mounting panel and receive runoff surgical waste fluid from near the drape fenestration, wherein the fluid collection device is configured to be selectively attachable to the mounting panel in either a first rotational orientation with respect to the mounting panel or a second rotational orientation different from the first rotational orientation with respect to the mounting panel, the mounting panel and the fluid collection device including geometric structural features for attaching the fluid collection device to the top surface of the mounting panel, wherein the fluid collection device is selectively attached substantially surrounding the seal by a user.

17. The surgical drape of claim 16, wherein a peripheral edge circumscribing the base panel fenestration, the intermediate panel fenestration, and the mounting panel fenestration is configured to be sealed to a patient.

18. The surgical drape of claim 16, wherein the intermediate panel has a surface area smaller than that of the base panel and the mounting panel has a surface area smaller than that of the intermediate panel.

* * * * *